United States Patent [19]

Nusbaum

[11] Patent Number: 6,013,435
[45] Date of Patent: Jan. 11, 2000

[54] DRUG RESISTANCE SCREENING METHOD USING MULTIPLEX AMPLIFICATION

[76] Inventor: Neil J. Nusbaum, 6 Irving La., New Hyde Park, N.Y. 11040

[21] Appl. No.: 08/537,259

[22] Filed: Sep. 29, 1995

Related U.S. Application Data

[63] Continuation of application No. 07/991,458, Dec. 15, 1992, abandoned, which is a continuation of application No. 07/580,767, Sep. 11, 1990, abandoned.

[51] Int. Cl.[7] .............................. C12Q 1/68; C12P 19/34; C07H 21/04
[52] U.S. Cl. ......................... 435/6; 435/91.2; 536/24.33
[58] Field of Search .............................. 435/6, 91.2, 91.1, 435/183, 270, 810; 436/63, 94, 501; 935/76, 77, 78; 536/24.33

[56] References Cited

U.S. PATENT DOCUMENTS

| | | | |
|---|---|---|---|
| 4,683,195 | 7/1987 | Mullis et al. | 435/6 |
| 4,800,159 | 1/1989 | Mullis et al. | 435/172.3 |
| 4,965,188 | 10/1990 | Mullis | 435/6 |
| 5,070,011 | 12/1991 | Parsons et al. | 435/6 |
| 5,075,212 | 12/1991 | Rotbart | 435/5 |
| 5,077,192 | 12/1991 | Liang et al. | 435/5 |
| 5,091,302 | 2/1992 | Newman et al. | 435/6 |
| 5,112,753 | 5/1992 | Renard et al. | 435/5 |
| 5,126,239 | 6/1992 | Livak et al. | 435/6 |

FOREIGN PATENT DOCUMENTS

| | | | |
|---|---|---|---|
| 88/03957 | 2/1988 | WIPO | C12Q 1/68 |

OTHER PUBLICATIONS

Bobo, Linda, et al.; "Diagnosis of *Chlamydia trachomatis* Cervical Infection by Detection of Amplified DNA with an Enzyme Immunoassay"; Journal of Clinical Microbiology, 1990, vol. 28, pp. 1968–1973.
Vilgalys, Rytas, et al.; "Rapid Genetic Identification and Mapping of Enzymatically Amplified Ribosomal DNA from Several Cryptococcus species"; Journal of Bacteriology, 1990, vol. 172, pp. 4238–4246.
Burg, Lawrence J., et al.; "Direct and Sensitive Detection of a Pathogenic Protozoan, *Toxoplasma gondii*, by Polymerase Chain Reaction"; Journal of Clinical Microbiology, 1989, vol. 27, pp. 1787–1792.
Sjöbring, Ulf, et al.; "Polymerase Chain Reaction for Detection of *Mycobacterium tuberculosis*"; Journal of Clinical Microbiology, 1990, vol. 28, pp. 2200–2204.
Moser, David R., et al.; "Detection of *Trypanosoma cruzi* by DNA Amplification Using the Polymerase Chain Reaction"; Journal of Clinical Microbiology, 1989, vol. 27, pp. 1477–1482.
Starnbach, Michael N., et al.; "Species–Specific Detection of *Legionella pneumophila* in Water by DNA Amplification and Hybridization"; Journal of Clinical Microbiology, 1989, vol. 27, pp. 1257–1261.
Waters, Andrew P., et al.; "Rapid, Sensitive Diagnosis of Malaria Based on Ribosomal RNA"; The Lancet, Jun. 17, 1989, vol. 1 for 1989, pp. 1343–1346.

Wakefield, A.E., et al.; "Detection of *Pneumocystis carinii* with DNA Amplification"; Medical Science, The Lancet, Aug. 25, 1990, vol. 336, pp. 451–453.
Olive, Michael D.; "Detection of Enterotoxigenic *Escherichia coli* after Polymerase Chain Reaction Amplification with a thermostable DNA Polymerase"; Journal of Clinical Microbiology, 1989, vol. 27, pp. 261–265.
Malloy, Diane C. et al.; "Detection of *Borrelia burgdorferi* Using the Polymerase Chain Reaction"; Journal of Clinical Microbiology, 1990, vol. 28, pp. 1089–1093.
Leong, Diane U.; "Design of a PCR Assay for the Rapid Detection of Bacteremia"; Infections in Medicine, 1992, vol. 9, pp. 43–48.
Matthews et al, Anal. Biochem., v.169. (1988) 1–25.
Chen et al. Dialog Abstract No. 7307792(File 73) FEMS Microbiol Lett., 1989, 57/1 (19–24).
Scanlon et al. J. Clin. Lab. Anal. 3:323–329 (1989).
Bloem et al. Nucleic Acids Res 18(9) 2830 (1990).
Frankel et al. Biosis Abstract No. 89072068 Mol Microbiol 3(12) 1729–34 (1989).
Halbert et al. Dialog Abstract 1295681 Clin Microbiol Newsletter; 10(5) 33–37 (1988).
Ng et al. Dialog Abstract No. 1181832 Antimicrob Agents Chemother 31(11) 1169–1174 (1987).
Arthur Michel, et al., "Detection of Erythromycin Resistance by the Polymerase Chain Reaction Using Primers in Conserved Regions of ern rRNA Methylase Genes", *Antimicrobial Agents and Chemotherapy*, Oct. 1990, 2024–2026.
Vliegenthart, John S., et al., "Identification of Three Genes Coding for Aminoglycoside–Modifying Enzymes by Means of the Polymerase Chain Reaction", *Journal of Antimicrobial Chemotherapy* (1990) 25, 759–765.
Scanlon et al., "Utility of the Polymerase Chain Reaction in Detection of Gene Expression in Drug–Resistant Human Tumors," Journal of Clinical Laboratory Analysis, vol. 3, pp. 323–329, 1989.
Nicolas et al., "Molecular Characterization of the Gene Encoding SHV–3 beta–lactamase Responsible for Transferable Cefotaxime Resistance in Clinical Isolates of _Klebsiella pneumoniae_," Antimicrobial Agents and Chemotherapy, vol. 33, No. 12, pp. 2096– , 1989.
Wiedmann et al., "The epidemiology of beta–lactamases," Journal of Antimicrobial Chemotherapy, vol. 24, Supplement B, pp. 1–22, 1989.

(List continued on next page.)

*Primary Examiner*—Kenneth R. Horlick
*Attorney, Agent, or Firm*—Morgan & Finnegan, L.L.P.; Kenneth H. Sonnenfeld; Stephen R. Smith

[57] ABSTRACT

Improved methods for assaying drug resistance and kits for performing such assays are disclosed. The methods comprise selectively amplifying target sequences associated with genetic elements which confer drug resistance and detecting and/or identifying the amplified target sequences. The methods are rapid and sensitive, and can be performed without isolating or culturing the organisms or cells being assayed.

56 Claims, No Drawings

OTHER PUBLICATIONS

Wolfson, "Quinolone Antimicrobial Agents: Adverse Effects and Bacterial Resistance," Eur. J. Microbiol. Dis., vol. 8, No. 12, pp. 1080–1092, Dec. 1989.

Laible et al., "Nucleotide sequences of the _pbpX_ genes encoding the penecillin–binding proteins 2x from _Streptococcus pneumoniae_ R6 and a cefotaxime–resistance mutant, C506," Molecular Microbiology, vol. 3, No. 10, pp. 1337–1348, 1989.

Dallas et al., "Polymerase Chain Reaction for Fast, Nonradioactive Detection of High– and Low–Risk Papillomavirus Types in Routine Cervical Specimens and in Biopsies," Journal of Medical Virology, vol. 27, No. 2, pp. 105–111, Feb. 1989.

Melchers et al., "Increased Detection Rate of Human Papillomavirus in Cervical Scrapes by the Polymerase Chain Reaciton as Comapred to Modified Fish and Southern–Blot Analysis," Journal of Medical Virology, vol. 27, No. 4, pp. 329–335, Apr. 1989.

Anceschi et al., "Multiple primer pairs polymerase chain reaction for the detection of human papillomavirus types," Journal of Virology Methods, vol. 28, No. 1, pp. 59–66, Apr. 1990.

Schochetman et al., "Polymerase Chain Reaciton," The Journal of Infectious Diseases, vol. 158, No. 6, pp. 1154–1157, Dec. 1988.

K. J. Scanlon et al., "Utility of the POlymerase Chai Reaction in Detection of Gene Expression in Druig–Resistant human Tumors," Journal of Clinical Laboratory Analysis, vol. 3, pp. 323–329, 1989.

M.–H. Nicolas et al., "Molecular Characterization of the Gene Encoding SHV–3 beta–latamase Responsible for Transaferable Cefotaxime resistance in Clinical isolates of _Klebsiella pneumoniae_," Antimicrobial Agents and Chemotherapy, vol. 33, No. 12, page, Dec. 1989.

B. Wiedemann et al., "The epidemiology of beta–lactamases," Journal of Antimicrobial Chemotherapy, vol. 24, Supplement B, pp. 1–22, 1989.

J. S. Wolfson, "Quinolone Antimicrobial Agents: Adverse Effects and bacterial Resistance," Eur. J. Microbiol. Dis., vol. 8, No. 12, pp. 1080–1092, Dec. 1989.

G. Laible et al., "Nucleotide sequences of the _pbpX_ genes encoding the pencillin–binding proteins 2x from _Streptococcus pneumonia_ R6 and a cefotaxime–resistant mutant, C506," Molecular Microbiology, vol. 3, No. 10, pp. 1337–1348, 1989.

DRUG RESISTANCE SCREENING METHOD USING MULTIPLEX AMPLIFICATION

This is a continuation of application Ser. No. 07/991,458, filed on Dec. 15, 1992, abandoned, which is a continuation of abandoned application Ser. No. 07/580,767, filed on Sep. 11, 1990.

FIELD OF THE INVENTION

The present invention relates to improved methods for determining the drug resistance of microorganisms. In particular, rapid methods for simultaneously screening for resistance to multiple drugs and kits utilizing the methods are disclosed. The methods of the present invention are especially useful for screening of microorganisms which are difficult to culture and also provide rapid screening for drug resistance at the earliest stages of infection, without the need to stop ongoing drug therapy. These screening methods are also useful for detecting the emergence of drug resistant microorganisms very early in its development, prior to any clinical manifestation of drug resistance or clinical evidence of therapy failure.

BACKGROUND OF THE INVENTION

Current methods of screening for drug resistance involve isolation and culturing of microorganisms from clinical specimens. When a sufficient culture is obtained, the isolated microorganisms are tested for sensitivity or resistance to a drug by their ability to grow in the presence of the drug (B. E. Murray (1990) Clinical Microbiology Reviews 3: 46–65). Growth of the microorganisms in the presence of a drug is indicative of resistance to that drug.

Such prior art methods are unsatisfactory in several respects. First, many significant pathogens are difficult to isolate from clinical specimens and/or difficult to culture in sufficient quantity to perform the standard drug resistance screening tests. In addition, such procedures can require several days since the microorganisms must first be cultured to obtain a sufficient number of cells, and then must be cultured again in the presence of the desired drugs to obtain a result. Often, the microorganisms must also be identified biochemically. A patient, particularly if marginally effective drug therapy has initially been instituted on an empirical basis, can deteriorate significantly while awaiting the results of such drug resistance screening. Further, the standard methods are relatively insensitive in detecting resistance due to their reliance on visible culture growth during the period of the assay. These methods are therefore only capable of demonstrating the existence of drug resistant organisms when the proportion of such microorganisms in the culture is sufficiently high to have a significant effect on visible culture growth. As a result, microorganisms are often erroneously characterized as susceptible to a drug, with potentially harmful consequences for the patient (See J. C. Pechere (1989) Eur. J. Cancer Clin. Oncol. 25: S17–S23, Supplement 2).

Microorganisms have developed a variety of mechanisms of resistance to drugs. These include, in part, the acquisition of genes which produce an enzyme capable of breaking down a particular drug (e.g., β-lactamases, conferring resistance to β-lactam antibiotics such as penicillin), cell membrane mutations which decrease permeation of the drug into the cell (e.g., altered membrane porins which confer resistance to quinolone antibiotics), and alterations in molecules which are the targets of the drugs so that interaction of the drug with its target is reduced (e.g., mutations in DNA gyrase conferring resistance to quinolones; alterations in penicillin-binding proteins providing resistance to β-lactam antibiotics).

Each of the many mechanisms of drug resistance is, ultimately, the result of genetic alteration which confers the resistant phenotype. Under the selective pressure applied by exposure to the drug, rare resistant microorganisms which arise in a sensitive population are able to survive and multiply, thus increasing their relative proportion compared to sensitive microorganisms. The genetic alteration or mutation can involve the acquisition of a plasmid or transposable element carrying a new gene which confers resistance, or it can involve mutation of a gene (usually chromosomal) coding for a normal component of the cell. Particularly in the case of plasmids and transposable elements, the acquired drug resistance can then be transferred to other microorganisms, either of the same species or of different species. As a result of such resistance transfer, there is often significant homology between the genes conferring resistance to a drug in different species of microorganisms.

For example, resistance to β-lactam antibiotics is known to be acquired by at least two genetic mechanisms: 1) acquisition of a gene coding for β-lactamase, and 2) alteration of one or more of the penicillin binding proteins in the cell membrane (J. C. Pechere (1989) Eur. J. Cancer Clin. Oncol. 25: S17–S22; R. Fontana et al. (1990) Eur. J. Clin. Microbiol. Infect. Dis. 9: 103–105; A. R. Wanger et al. (1990) The Journal of Infectious Diseases 161: 54–58; C. E. Nord (1990) Reviews of Infectious Diseases 12: S231–S234).

Resistance to the quinolones is also known to be mediated by several genetic mechanisms, including: 1) mutations in the genes coding for either of the two subunits of DNA gyrase (the gyrA and gyrB genes), 2) mutations in one or more genes for the outer membrane porins, and 3) altered outer membrane lipopolysaccharides (LPS) (D. C. Hooper et al. (1989) The American Journal of Medicine 87: 6C-17S-6C-23S; J. S. Wolfson (1989) Eur. J. Clin. Microbiol. Infect. Dis. 8: 1080–1092; C. S. Lewin et al. (1990) J. Med. Microbiol. 31: 153–161; J. S. Wolfson et al. (1989) Reviews of Infectious Diseases 11: S960–S978).

Macrolide-lincosamide-streptogramin B resistance, which includes resistance to Clindamycin and Erythromycin, is mediated by acquisition of a gene for an RNA methylase which methylates 23S rRNA so that the drug is no longer bound. These genes (ermF and related sequences) are highly homologous in all of the bacterial species tested, although they can exist either on plasmids or as chromosomal elements (M. Halula et al. (1990) Reviews of Infectious Diseases 12: S235–S242). The ermF like sequences are often associated with a genetic element conferring resistance to tetracycline (tetF).

The polymerase chain reaction ("PCR") has been a significant development in genetic analysis, allowing amplification of minute amounts of a specified gene sequence (U.S. Pat. No. 4,683,195; U.S. Pat. No. 4,683,202; U.S. Pat. No. 4,800,159; B. I. Eisenstein (1990) The New England Journal of Medicine 322: 178–182; G. Schochetman et al. (1988) The Journal of Infectious Diseases 158: 1154–1157). In this method, a pair of single stranded oligonucleotide primers, each complementary to sequences on opposite strands of the target DNA, are selected to encompass the target sequence to be amplified and define the two ends of the amplified stretch of DNA. After separating double stranded DNA and annealing the primers to the 3' end of the target sequence on each strand, two complementary second strands are synthesized by extension of the annealed primers using a DNA polymerase, ie. a new single strand of DNA is synthesized for each annealed primer. These newly synthesized DNA's, as well as the original DNA sequence, can then be used for a second cycle of primer annealing and DNA synthesis. Accordingly, the desired target DNA sequence is amplified geometrically with each repetition of the cycle. Typically, within a few hours a target DNA sequence can be amplified 100,000 fold, particularly when automated methods are used to perform the cyclic reactions.

The polymerase chain reaction can also be used to specifically amplify only those target sequences which are expressed, ie., those which are transcribed. To do so, mRNA is isolated and cDNA is made from the RNA using reverse transcriptase. The cDNA, which represents the expressed genes, is then used as target DNA in the PCR amplification reaction.

Because of its high sensitivity and specificity, PCR has been successfully used as a means for identifying microorganisms and viruses in the diagnosis of infectious disease (B. I. Eisenstein (1990) J. Infectious Diseases 161: 595–602; L. Shih et al. (1990) J. Medical Virology 30: 159–162; A. R. Lifson et al. (1990) J. Infectious Diseases 161: 436–439; M. M. Anceschi et al. (1990) J. Virological Methods 28: 59–66). PCR amplification has been used to detect changes in expression of the dTMP synthase gene (ie., changes in the level of mRNA) associated with drug resistance in human tumors (K. J. Scanlon (1989) J. Clinical Laboratory Analysis 3: 323–329; M. Kashani-Sabet et al. (1988) Cancer Research 48: 5775–5778). PCR has also been used to analyze point mutations in HIV-1 reverse transcriptase which confer resistance to AZT (B. A. Larder et al. (1989) Science 246: 1155–1158) and point mutations in the dihydrofolate reductase-thymidylate synthase gene associated with pyrimethamine resistance in Plasmodium falciparum (A. F. Cowman et al. (1988) PNAS 85: 9109–9113; J. W. Zolg et al. (1989) Molecular and Biochemical Parasitology 36: 253–262; M. Tanaka et al. (1990) Molecular and Biochemical Parasitology 39: 127–134; J. W. Zolg et al. (1990) Molecular and Biochemical Parasitology 39: 257–266).

The above publications utilize the known PCR amplification method, in which a single pair of primers is used in each PCR reaction to amplify a target sequence representing a single gene. This method is usually adequate for research studies in which information about a particular gene is sought. However, it is not practical for detection of resistance to a drug in a clinical setting because resistance to a single drug can potentially involve any of several genetic elements corresponding to the multiple mechanisms of resistance to the drug. A clinical laboratory must also screen each clinical specimen for resistance to many drugs, each of which can be mediated by multiple genetic mechanisms. In such a setting, performing separate, sequential, PCR reactions (e.g., as disclosed in U.S. Pat. No. 4,683,195, U.S. Pat. No. 4,683,202 and U.S. Pat. No. 4,800,159) to detect each genetic element associated with resistance would be an expensive and time consuming procedure. The advantages of speed and simplicity associated with PCR would be lost by performing such individual assays on the scale required for drug resistance screening in a clinical laboratory.

The present invention improves upon several significant shortcomings of prior art drug sensitivity screening methods, namely 1) the unsatisfactory length of time involved in obtaining a result, 2) the fact that resistant microorganisms must comprise a significant portion of the microorganisms in order to be detected, and 3) the need to stop drug therapy to perform drug resistance screening. The inventive method utilizes simultaneous amplification of genetic elements specifically associated with drug resistance, which reduces expense and provides rapid screening. Multiple primer pairs, each specific for a genetic element associated with a particular mechanism of resistance to a drug, provide the basis for simultaneous amplification of the desired genetic elements. The inventive methods can be used to 1) identify, in a single simultaneous screening, the presence of potential resistance to a drug which is mediated by multiple genetic elements, or 2) to simultaneously screen for the presence of potential resistance to multiple drugs.

The particular advantages of the inventive method reside in the fact that it is not necessary to isolate or identify a microorganism prior to screening for drug resistance. Generally, for purposes of making a rapid, informed decision regarding selection of a drug for treatment of an infection, such specific information is not immediately required. It is usually of primary importance to know only whether a drug of choice is likely to be therapeutically effective, regardless of the etiology of the infection. The methods of simultaneous amplification of specific genetic elements of the present invention are capable of providing such information in a short period of time, and therefore allow more rapid initiation of therapy.

SUMMARY OF THE INVENTION

For purposes of making a rapid initial decision regarding the drug to be used in treating an infection, the physician generally does not need to know the identity of the pathogen or pathogens responsible for the infection. The information which is critical, particularly in the case of serious or life threatening infection, is which of the drugs being considered for therapy are most likely to be effective. That is, the physician needs to know, prior to initiating drug therapy, whether or not resistance to a particular drug or series of related drugs is present in the population of microorganisms responsible for the infection, regardless of their species. The present methods and kits provide an aid to clinical decision making earlier in the development of drug resistance than is currently possible using standard drug resistance screening techniques.

The present invention is capable of providing this important information much more rapidly than prior art methods, due to the elimination of the time consuming steps of isolating, culturing and identifying microorganisms from clinical specimens. The inventive methods also allow detection of the development of drug resistance at its earliest emergence, long before drug resistance would be detected as culture growth in the presence of the drug during the standard assay period. Thus, the clinician will be able to monitor the progress of drug therapy more closely and make a decision to change drug treatment well before the clinical condition of the patient deteriorates as a result of emergence of resistant microorganisms.

The inventive methods are capable of simultaneously detecting multiple genetic elements associated with resistance to a drug, and comprise a) providing a test sample comprising nucleic acid isolated from a clinical specimen, b) providing multiple pairs of single stranded oligonucleotide primers selected so that the oligonucleotides of each pair are complementary to the 3' ends of one of multiple double stranded DNA target sequences associated with resistance to the drug, c) combining the primer pairs with the test sample under conditions such that each primer pair will hybridize sufficiently specifically to its target sequence that any nonspecific hybridization will not prevent detection of target sequences associated with resistance to the drug, d) treating the hybridized primers under conditions such that primer extension products are simultaneously synthesized for all sequences to which a primer is hybridized, e) repeating steps c) and d) until the target sequences present are sufficiently amplified to be detected, and f) detecting the amplified target sequences.

In an alternative embodiment, the inventive method is used for simultaneously detecting genetic elements associated with resistance to multiple drugs. This method comprises a) providing a test sample comprising nucleic acid isolated from a clinical specimen, b) providing multiple pairs of single stranded oligonucleotide primers selected so that the oligonucleotides of each pair are complementary to the 3' ends of one of multiple double stranded DNA target sequences associated with resistance to the drugs, c) combining the primer pairs with the test sample under conditions such that each primer pair will hybridize sufficiently specifically to its target sequence that any nonspecific hybridization will not prevent detection of target sequences associated with resistance to the drugs, d) treating the hybridized primers under conditions such that primer extension products are simultaneously synthesized for all sequences to which a primer is hybridized and the predicted primer extension products associated with resistance to each drug are separately identifiable, e) repeating steps c) and d) until the target sequences are sufficiently amplified to be detected, f) detecting the amplified target sequences, and h) identifying the amplified target sequences.

The drug resistance screening methods of the invention utilize a gene amplification reaction similar to the polymerase chain reaction ("PCR"). However, unlike prior art PCR reactions, the present invention employs multiple pairs of primers to initiate the simultaneous amplification of multiple genetic elements associated with drug resistance, using genetic material obtained from clinical specimens. The primer extension products resulting from the amplification are then detected and identified. The amplification of a genetic element associated with resistance to a particular drug indicates the presence of that element in the specimen. The indicated drug therefore may not be therapeutically effective or may exert selective pressure which could cause the failure of long term therapy.

The inventive methods are applicable to any genetic element associated with drug resistance for which a unique sequence is known, whether it resides on a drug resistance plasmid, is present in a chromosome, or is associated with a transposable element. The cyclic amplification reactions can be performed by hand or, preferably, can be automated.

The particular uses and advantages of the invention include, in part: 1) rapid analysis of drug resistance patterns directly from clinical specimens, 2) rapid analysis of the epidemiology of drug resistance in a hospital environment or in patients receiving long term drug therapy, either by screening individual patients or pooled specimens from several patients in a particular area of the hospital, 3) analysis of drug resistance patterns without the need to stop ongoing drug therapy, 4) early detection of drug resistance in patients who have undergone invasive procedures and who are at special risk of infection (e.g., ICU patients), 5) early detection in other high risk patients for whom the development of drug resistant infections pose a particular risk (e.g., AIDS patients, bone marrow transplant recipients, patients receiving cytotoxic chemotherapy, and other immunosuppressed patients), 6) when required, the ability to test simultaneously for drug resistance patterns and identify the microorganism or microorganisms involved, 7) detection of the emergence of drug resistance during therapy at its earliest stages, well before such resistance is detectable as visible culture growth, thus allowing a change in therapy before the patient's clinical condition deteriorates, and 8) sensitive detection of the emergence of resistance to a less toxic drug, allowing a more toxic drug to be used later during therapy if necessary, thus reducing the patient's exposure to the more toxic drug.

The methods of the present invention are also applicable to screening for antibiotic resistance in animals, for example to guide selection of prophylactic antibiotic therapy in a veterinary practice. This can be accomplished either by screening individual animals or as a surveillance method for a herd by screening pooled specimens from several animals.

The present invention also contemplates kits which contain the reagents used in the practice of the inventive methods. The kits comprise, in a convenient package, the reagents used in simultaneous screening for multiple mechanisms of resistance to a single drug and/or the reagents used in simultaneously screening for resistance to multiple drugs, i.e., multiple pairs of single stranded oligonucleotide primers selected so that the oligonucleotides of each pair are complementary to the 3' ends of one of multiple double stranded DNA target sequences associated with drug resistance, and reagents for DNA synthesis, whereby treatment of a test sample containing nucleic acid with the primers and the reagents results in hybridization of each primer pair to its target sequence and simultaneous amplification of the target sequences to which primers are hybridized.

In an alternative embodiment, the kits further comprise reagents for simultaneously identifying a microorganism or microorganisms present in the clinical specimen. For example, a diagnostic kit for screening for resistance to a drug can comprise, in the same package, primers specific for microorganisms typically resistant to the drug as well as primers specific for genetic elements associated with the various mechanisms of resistance independent of the species of the resistant microorganism.

DEFINITIONS

As used herein, the following terms have the indicated meanings:

Mechanism of drug resistance—The means by which resistance to a drug is mediated, e.g. reduced permeation of the drug into a cell. A mechanism of resistance can be associated with a single genetic element (e.g., acquisition of an enzyme) or with multiple genetic elements (e.g., alteration of membrane proteins).

Genetic element—A gene, or a group of related genes containing regions of sequence homology and coding for similar functions, which are associated with development of resistance to a drug or group of related drugs.

Oligonucleotide primer or primer—A small, single stranded DNA molecule having a sequence which is complementary to a DNA sequence contained in a genetic element. A pair of oligonucleotide primers is selected so that the members of the pair hybridize to complementary sequences on opposite strands of a double stranded genetic element in such a way that DNA synthesis primed by the primers produces two complementary strands of DNA representing the region of the genetic element bounded by the hybridized primer pair. Hybridization of primers to complementary sequences must be sufficiently specific that any DNA synthesis primed from nonspecifically hybridized primers does not prevent detection and/or identification of the correct primer extension products.

Target sequence—The segment of DNA bounded by hybridized oligonucleotide primer pairs. The target sequence can comprise a full length genetic element or a portion thereof.

Primer extension product, amplification product, amplified target sequence—The multiple complementary copies of a target sequence, resulting from DNA synthesis primed by hybridized oligonucleotide primers.

Specific hybridization—Hybridization of an oligonucleotide to its correct complement.

Nonspecific hybridization—Hybridization of an oligonucleotide to a related sequence which is not its correct complement.

Detectable label—A molecule or moiety which can be used to produce a detectable signal, either directly (e.g., radioisotopes or fluorescent labels) or in combination with additional reagents (e.g., biotin, avidin, and chromogenic enzymes).

DETAILED DESCRIPTION OF THE INVENTION

In the present inventive methods, DNA amplification techniques are improved and adapted to provide rapid, simultaneous screening for resistance to multiple drugs and/or simultaneous screening for multiple genetic mechanisms associated with resistance to a single drug. Specifically, nucleic acid amplification is performed using nucleic acid derived from a clinical specimen and multiple pairs of primers, each pair being capable of hybridizing to one of the genetic elements of interest. Following amplification of any target sequences complementary to the primers which are present in the clinical specimen, the amplified sequences are detected and identified to reveal the corresponding drug resistance phenotype. The products of amplification can be identified using any means capable of discriminating between the amplification products associated with each drug resistance or microorganism being assayed. These include, for example, agarose gel electrophoresis with ethidium bromide (EthBr) staining, Southern blotting (Southern, E. 1975. J. Mol. Biol. 98:503.), "dot blotting" (Grunstein, M. and Hogness, D. 1975. PNAS 72:3961.), fluorescence assays, and nucleic acid hybridization methods known in the art.

The nucleic acid amplification reactions are preferably performed using clinical specimens suspected of containing infectious agents, however, it will be apparent to those skilled in the art that the inventive methods are applicable to testing for drug resistance developed by any type of cell. The specimens can be blood samples, tissue samples, urine, sputum, throat swabs, exudates or other clinical specimens normally tested in the diagnosis of infection. Although it is not always required, it is preferable to at least partially purify nucleic acid from the specimen prior to amplification in order to obtain optimal efficiency of the amplification reactions. For example, after disruption of cells in the specimen, nucleic acid can be extracted from contaminating cell debris and other protein substances by extraction of the sample with phenol. In phenol extraction, the aqueous sample is mixed with an approximately equal volume of redistilled phenol and centrifuged to separate the two phases. The aqueous phase, containing the nucleic acid, is removed and precipitated with ethanol to yield nucleic acid free of phenol for use in the amplification reactions. Alternatively, target DNA can be purified according to the method of Vogelstein and Gillespie (PNAS 76:615, 1979).

The sample for nucleic acid amplification, which potentially contains amplifiable target sequences, can be single or double stranded DNA or RNA. Since some genetic elements associated with drug resistance may be present but unexpressed, in some cases it is desirable to amplify only those genetic elements which are expressed, i.e., transcribed into mRNA. In this way, "silent" resistance elements are not detected in the assay. When RNA is to be amplified to assay for expressed genetic elements associated with drug resistance, mRNA is isolated from the clinical specimen and a cDNA copy of the RNA is synthesized using reverse transcriptase prior to performing the amplification reactions.

Each of the multiple pairs of primers selected for use in the present amplification reactions is designed to hybridize with a target sequence associated with a genetic element involved in the development of drug resistance. In an alternative embodiment, the pairs of primers additionally include primers capable of hybridizing with target sequences characteristic of a specific microorganism. Typically, this is a microorganism which is known to be frequently resistant to a drug being considered for therapy.

In a first embodiment, primer pairs are selected so as to hybridize to acquired genetic elements associated with the drug resistance. These genetic elements are absent in sensitive microorganisms. For example, the β-lactamase genes which have been identified and sequenced have been found to be highly homologous in different species, regardless of whether they are present in the chromosome or on an extra-chromosomal genetic element (B. Wiedemann et al. (1989) J. Antimicrobial Chemotherapy 24: 1–22; K. Bush (1989) Antimicrobial Agents and Chemotherapy 33: 259–263). Therefore, by comparing the sequences, two regions of the gene can be selected which are homologous in all or most of the β-lactamase genes. These regions are selected so as to be suitable for the hybridization of complementary primer pairs and amplification of the portion of the gene bounded by the two sequences (the target sequence). That is, the sequences are not only homologous in as many β-lactamase genes as possible, they are situated an appropriate distance apart in the genetic element to permit amplification and subsequent detection and/or identification of the amplification product. Similarly, by determining regions of sequence homology between the various ermF like sequences indicating resistance to clindamycin/erythromycin, primer pairs can be designed which will hybridize to ermF and related sequences regardless of the bacterial species. When one pair of primers cannot be designed to hybridize with all of the related genetic elements, additional primer pairs homologous with the remainder are designed in a similar manner.

In a second embodiment, primer pairs are selected to hybridize to drug resistant mutant forms of genetic elements which otherwise code for normal cellular proteins. For example, sequence analysis of genetic elements coding for β-lactam resistant penicillin binding proteins (PBP) and comparison of the sequences obtained with wild-type sensitive PBP genes can be used to identify the mutations which are responsible for resistance by this mechanism. Using this information, primer pairs can be selected which will hybridize sufficiently specifically to the mutated gene sequences that any nonspecific hybridization to wild-type PBP gene sequences will not prevent detection and/or identification of the amplification product of the mutant genetic element. Similarly, the sequences of mutant genes conferring resistance to quinolone antibiotics can be compared to the sequences of wild type genetic elements coding for sensitive proteins. Primer pairs which can specifically hybridize to each such mutation and which are suitable for use in the amplification reaction can then be designed and used to simultaneously amplify all quinolone resistance-associated target sequences present in DNA derived from a clinical specimen. Optimization of the amplification reaction to obtain sufficiently specific hybridization to the mutant genes is well within the skill in the art, and is preferably achieved by adjusting the annealing temperature.

Each primer of a pair is a single stranded oligonucleotide, usually 15–30 bases long, which is complementary to a sequence at the 3' end of one of the strands of a double stranded DNA target sequence. Each pair comprises two such primers, one of which is complementary to one 3' end and the other of which is complementary to the other 3' end of the target sequence. The target sequence is generally about 10–1,500 base pairs long, but can be as large as 3–4 Kb. When hybridized to their complements in the target sequence, the primers are capable of serving as starting points for synthesis of DNA primer extension products using a DNA polymerase and deoxyribonucleoside triphosphates (dNTP's). If the target sequences are single stranded, initial hybridization of one oligonucleotide of a primer pair allows synthesis of the complementary strand which contains the complement of the other oligonucleotide of the primer pair. Subsequent cycles of amplification then proceed as for double stranded target sequences.

The primers can be synthesized using any of the known methods of oligonucleotide synthesis (e.g., the phosphodiester method of Agarwal et al. 1972. Agnew. Chem. Int. Ed. Engl. 11:451, the phosphotriester method of Hsiung et al. 1979. Nucleic Acids Res. 6:1371, or the automated diethylphosphoramidite method of Beaucage et al. 1981. Tetrahedron Letters 22: 1859–1862), or they can be isolated fragments of naturally occurring or cloned DNA. In one embodiment, the primers can be derivatized to include a detectable label suitable for detecting and/or identifying the primer extension products (e.g., biotin, avidin, or radiolabeled dNTP's), or with a substance which aids in the isolation of the products of amplification (eg. biotin or avidin). To avoid self hybridization of a primer pair, each pair preferably contains not more than two bases which are complementary to each other, especially at their 3' ends. Sequences which provide possibilities for formation of internal secondary structure also are preferably avoided in designing the primers. A G+C content ranging from about 40% to about 60% is preferable for optimum hybridization.

The sequences of the oligonucleotides of each primer pair are selected so that each oligonucleotide will hybridize to one of the two strands of a target sequence associated with a mechanism of resistance to a particular drug. Multiple primer pairs are selected to provide hybridization to all of the target sequences associated with resistance. Preferably, if possible, the primer sequences are selected to hybridize to a segment of a genetic element which is not only unique but substantially homologous in a variety of species of microorganisms exhibiting the associated mechanism of resistance, thus reducing the number of specific primer pairs which are required for complete drug resistance screening.

When multiple mechanisms of resistance to a particular drug are known, a pair of primers capable of hybridizing to each associated target sequence is included simultaneously in the amplification reaction. Again, it is preferable, when the nature of the target sequences allow, to select primer sequences which hybridize to segments of the genetic elements which are not only unique but also substantially homologous between species of microorganisms exhibiting that genetic element.

In another embodiment, in addition to the primer pairs specific for detection of mechanisms of drug resistance as described above, the amplification reaction can include primer pairs which hybridize to genetic elements which are characteristic of a particular genus and/or species of microorganism. Inclusion of such primers provides the added advantage of detecting the presence of certain microorganisms in the specimen which are frequently resistant to the drug of interest or which are known to readily develop such resistance upon exposure to the drug. Detection of these microorganisms could be useful in clinical decision-making as well, even if specific drug resistance is not detected, particularly if long term therapy is contemplated.

The amplification reaction begins with denaturation of the target DNA, if it is double stranded, using heat, enzymes such as helicase, or chemical means. An excess of each of the multiple primer pairs is then hybridized (i.e., annealed) to the single stranded template at a temperature selected to provide optimal specificity of hybridization of each primer to its correct target sequence. The primer extension products, which are complementary to the separated strands of the target sequence, are then synthesized in the presence of the four deoxyribonucleoside triphosphates (dNTP's) and a DNA polymerase such as the Klenow fragment of $E.$ $coli$ polymerase I, T4 polymerase, or Taq polymerase. The denaturing, annealing and synthesis steps are repeated, preferably for approximately 10 to 45 cycles, or as required, until amplification of the target sequences is sufficient for detection and/or identification.

The amplification reaction is preferably performed using an automated apparatus such as the DNA Thermal Cycler for PCR (available from Perkin-Elmer Cetus) according to the procedures recommended by the manufacturer. Briefly, the reaction is preferably performed in a small volume, preferably about 100 Al in a 0.5 ml microcentrifuge tube, with a 50–100 $\mu$l cap of mineral oil to prevent evaporation. The buffer consists of approximately 50 mM potassium chloride, 10 mM Tris-HCl pH 8.3, 1.5–4.0 mM magnesium chloride, 0.001% w/v gelatin, 200 $\mu$M of each of the four dNTP's, an excess of primers, and 1.0–3.0 units of Taq DNA polymerase. The target DNA is denatured at 92–95° C. for approximately 1 min. The primers are then hybridized to the target DNA at 37–55° C. for approximately 1 min., followed by a primer extension step at approximately 72° C. for 2 min. The cycle of denaturation, hybridization and synthesis is repeated to obtain amplification of the desired sequences and, when reaction conditions are optimized, can result in a 100,000-fold to 1,000,000-fold amplification of target sequences. Optimization of the reaction conditions to obtain maximum amplification of the target sequences is well within the skill in the art and is the subject of several publications (H. A. Ehrlich, ed. *PCR Technology: Principles and Applications for DNA Amplification*; M. A. Innis et al. *PCR Protocols: A Guide to Methods and Applications*).

The primer extension products are preferably separated from primers and unincorporated nucleotides following amplification. This is preferably accomplished by performing a separation according to molecular weight or size (e.g., using Centricon Micro-Concentrators available from Amicon). Next, when it is desired to separately isolate the amplification products associated with resistance to each of two drugs, and the respective sets of primers have been labeled with biotin and avidin, the two amplification products can be separated by binding to avidin and biotin, respectively. In an alternative embodiment, the amplification products associated with resistance to each of two or more drugs can be separated by size without first removing primers and dNTP's. This can be accomplished, for example, by gel filtration chromatography or gel electrophoresis, so that the smaller primers and dNTP's are removed simultaneously with the separation of extension products.

The primer extension products obtained by simultaneous amplification of the target sequences associated with drug resistance can be detected and identified in a variety of ways, depending on the type of information desired. In one embodiment, a detectable label is used to detect the products of the amplification reaction. Labels which are suitable for detecting nucleic acids, either directly or indirectly, are well known in the art and include, for example, biotin, avidin, radioactive labels, enzymes, and fluorescent molecules. The desired label, which can also be a component of a multi-component detection system, can be: 1) incorporated into the primers prior to performing the amplification reaction; 2) incorporated into the primer extension products during the amplification reaction in the form of one or more labeled dNTP's, or; 3) added after the amplification to indirectly detect primer extension products. In an alternative embodiment, if they are produced in sufficient quantity, the primer extension products can be visualized after their synthesis by staining with an intercalating dye such as ethidium bromide (EthBr).

Incorporation of radioactively labeled dNTP's into primer extension products during the amplification reaction can be used to directly detect amplification products. For indirect detection, hybridization of unlabeled amplification products with probes radioactively labeled with $^{32}P$, $^{14}C$ or $^{3}H$ can be used to detect a positive result in Southern blots or dot blots. The primers used in the amplification reaction itself are often convenient probes for this and other hybridization methods. However, other oligonucleotides can also be used as probes, as is known in the art, as long as they contain sequences which are capable of specifically hybridizing to the products of the amplification.

In another embodiment, a biotin/avidin detection system can be used to detect primer extension products. In this system, the primers and/or one or more of the dNTP's incorporated during amplification are labeled with biotin. The primer extension products are detected by binding of an avidin or streptavidin conjugate to the biotin. The conjugate comprises avidin or streptavidin conjugated to a detectable label such as a chromogenic enzyme (e.g., alkaline phosphatase or horse radish peroxidase) or a fluorescent molecule. Binding of avidin or streptavidin conjugate to biotin in the primer extension products is detectable by increased fluorescence or by the formation of a colored enzyme reaction product, either in solution or in a dot blot or Southern blot format. The positions of the biotin and avidin can also be reversed. That is, the primer extension products can be labeled with avidin which binds enzyme or fluorescent labeled biotin. Anti-biotin antibody conjugated to the detectable label can be used as an alternative to avidin or streptavidin for detection of primer extension products containing incorporated biotin.

When indirect detection of primer extension products is desired using avidin and biotin, the primer extension products preferably contain no derivatized dNTP's and are detected by hybridization to biotin or avidin labeled primers or probes in a dot blot or Southern blot format. The hybridized probes are then detected using labeled biotin, avidin, anti-biotin or anti-avidin as appropriate.

Primer extension products can also be detected by incorporation of an intercalating dye such as ethidium bromide (EthBr). Preferably, this is accomplished by subjecting the products of amplification to agarose gel electrophoresis in the presence of EthBr, or staining with EthBr after gel electrophoresis. Electrophoresis is performed under conditions such that the bands containing primer extension products are separated from each other and from unextended primers and unincorporated dNTP's. Detection of bands of fluorescence in the gel under ultraviolet light indicates a positive amplification reaction.

When the screening test is designed to detect resistance to a single drug, each of the multiple pairs of primers employed in the amplification reaction is preferably capable of specifically hybridizing to one of the various genetic elements involved in the different mechanisms of resistance to the drug. When it is not necessary to know which mechanism of resistance is present in the population, primer extension products can be detected without regard to which primer extension product is responsible for producing the positive response in the assay. A "dot blot" type of detection system is particularly useful in this type of assay because it is simple to perform and provides rapid results when separate identification of primer extension products is not required. Detection of primer extension products in a "dot blot" format preferably makes use of a chromogenic enzyme, but can also utilize radioactive or fluorescent detection methods.

When it is desired to screen simultaneously for resistance to multiple drugs using the methods of the invention, primer pairs selected to be capable of specifically hybridizing to the genetic elements involved in each of the mechanisms of resistance to each drug of interest in the assay are included simultaneously in the amplification reaction. In such a case, it is preferable to be able to separately identify the amplification products associated with resistance to each drug. This can be accomplished, for example, by selecting the primer pairs which hybridize to target sequences associated with resistance to each drug so that the primer extension products are sufficiently different in size to be separately identified, for example, as separate bands on gel electrophoresis or separable by size or molecular weight using other means known in the art. By this it is meant that, in the detection system being used, the primer extension products associated with each drug resistance being tested should be distinguishable from those of any other drug resistances being tested. For example, if the primer extension products will be analyzed by gel electrophoresis, with or without Southern blotting, the position of hybridization of the primer pairs to the target sequences associated with each drug resistance should be selected so that any extension products generated can be separated by size on the gel from those associated with resistance to other drugs. If a sufficient amount of primer extension product is produced by the amplification reaction, the bands on the gel can be detected directly by staining with EthBr and visualization under ultraviolet light. The size of the primer extension products in each band can be determined by comparison with molecular weight standards. It is not necessary that primer extension products associated with resistance to the same drug be separable unless it is desired to determine which of the mechanisms of resistance is present.

Alternatively, when resistance to multiple drugs is being simultaneously detected, different labeling systems can be employed to identify the extension products associated with each drug resistance. For example, the primers or extension products associated with each drug resistance can be detected directly (by incorporation of a label) or indirectly (by hybridization with labeled probes) using different radioisotopes which are separately identifiable on scintillation counting by their radioactive emission spectra (e.g., $^{32}$P and $^{3}$H). The presence of primer extension products associated with each type of drug resistance can also be detected on dot blots or Southern blots using chromogenic enzyme labels which produce reaction products of different colors (eg. alkaline phosphatase and horse radish peroxidase). Detection can either be performed directly by binding of enzyme label to biotin and avidin which is incorporated into the extension products or indirectly through hybridization of avidin and biotin-containing probes. The primer pairs representing resistance to each drug can also be derivatized with labels which allow separate purification of the amplification products, such as avidin on one set of primers (purified by binding to biotin) and biotin on another set of primers (purified by binding to avidin). Such separate identification methods are also applicable, but usually not necessary, when screening for multiple mechanisms of resistance to a single drug, since identification of a particular mechanism of resistance to a drug is not usually a factor in the immediate therapeutic decision. Detection of potential resistance to the drug, regardless of the genetic mechanism, will usually be sufficient to contraindicate its use.

The reagents and devices used in practicing the invention can be packaged in the form of a test kit for convenient commercialization and use. Preferably, a kit comprises multiple primer pairs as described above and reagents for performing the desired amplification reaction. For example, a kit for screening for multiple mechanisms of resistance to a single drug can comprise primers which hybridize to the target sequences associated with the various mechanisms of resistance to that drug as disclosed above, the four dNTP's, a DNA polymerase and concentrated amplification buffer. A kit for screening for resistance to multiple drugs can comprise primers which hybridize to the target sequences associated with the various mechanisms of resistance to each drug as disclosed above, the four dNTP's, a DNA polymerase and concentrated amplification buffer. In another embodiment, the kit further comprises primers or other probes derivatized with a detectable label for use as probes for detecting and/or identifying amplified target sequences.

When the means for detecting amplified target sequences involves a detectable label, the primers and/or at least one dNTP are derivatized with the detectable label. When the detectable label is a component of a multicomponent detection system, the kit further comprises the remaining components of the detection system, such as substrates and reagents for enzyme reactions, labeled biotin, labeled avidin.

The test kits of the invention can further comprise any of the following components for additional convenience: DNA known to contain the target sequences of interest (positive control) and/or DNA known to be free of the target sequences of interest (negative control), means for preparation of the test sample, tubes or receptacles for preparation of the sample or performing the amplification reaction, means for detecting amplified target sequences, and means for identifying amplified target sequences either by size or using different detectable labels. The means useful in detecting and/or identifying amplified target sequences are disclosed in detail above, and include both detectable labels, reagents, and devices, any of which can be included in the kits of the present invention. Such components can include, for example, materials for performing dot blots or Southern blots, materials for performing gel electrophoresis, means for lysing cells and extracting nucleic acid, etc.

The inventive methods disclosed herein can be routinely and rapidly performed by laboratory personnel, particularly if automated procedures are used. Due to the rapidity and sensitivity of the methods, it is possible to detect drug resistance before it is clinically manifested and becomes a significant problem in patient management. Also, the inventive methods make it practical to routinely monitor patients who are at high risk of developing drug resistance and who are particularly susceptible to uncontrolled infections.

The following examples illustrate certain embodiments of the present invention, but should not be construed as limiting its scope in any way. It is understood that the examples are simulated and prophetical rather than representative of work actually done. Of course, certain modifications and variations will be apparent to those skilled in the art from the teachings of the foregoing disclosure and the following examples, and these are intended to be encompassed by the spirit and scope of the invention.

EXAMPLE 1

Detection of Resistance to β-Lactam Antibiotics and the Presence of Pseudomonas

Preparation of the Clinical Specimen

Target DNA is extracted from a clinical specimen by lysing the cells. The DNA released is then extracted from the cell debris by phenol extraction and ethanol precipitation. The DNA sample is concentrated prior to performance of the amplification reaction by resuspending the precipitate in a reduced volume of reaction buffer, i.e., 100 μl of reaction mixture.

Selection and Synthesis of Primers

The following genes coding for β-lactamase are compared and regions of homology identified:

1. Nicolas et al. (1989) Antimicrobial Agents and Chemotherapy 33: 2096–2100. The SHV-3 gene of *K. pneumoniae*, conferring resistance to cefotaxime. The gene is 92% homologous to the LEN-1 gene of *K. pneumoniae* which codes for another β-lactamase.
2. Thompson et al. (1990) Journal of Bacteriology 172: 2584–2593. The cfiA gene of *B. fragilis* TAL 2480, conferring resistance to cefoxitin and imipenem.
3. Arakawa et al. (1989) Antimicrobial Agents and Chemotherapy 33: 63–70. A β-lactamase gene from *K. oxytoca* E23004 which confers resistance to cefoperazone and aztreonam, and also hydrolyzes many other cephalosporins.

A primer pair is selected for each gene so that the expected amplified target sequence is about 600 nucleotides in length.

Similarly, the sequence of a gene coding for cefotaxime resistant PBP 2X from *Streptococcus pneumoniae* is analyzed to identify the mutations associated with the resistant phenotype (Laible et al. (1989) Molecular Microbiology 3: 1337–1348). Three nucleotide substitutions, resulting in three amino acid changes are associated with the resistant gene. These mutations are Met 289 to Threonine, Glycine 597 to Aspartate and Glycine 601 to Valine. The primer pair is selected so that one member of the pair will hybridize to a portion of the wild type sequence and the other member of the pair is specific for the mutations at amino acid positions 597 and 601, resulting in an amplified target sequence of about 600 nucleotides.

In addition, the AlgR3 gene of *P. aeruginosa* (Kato et al. (1990) PNAS 887: 2887–2891) was analyzed for selection of primers. This gene is involved in alginate synthesis and the amino acid sequence shows no significant similarity to other bacterial proteins. The primer pair is selected so that the expected amplification product will be approximately 68 nucleotides long.

Following identification and selection of the appropriate sequences for primer pair design, the following primer pairs are synthesized and purified according to the diethylphosphoramidite method of Beaucage et al.:

1. SHV-3:
   Primer 1, nt 221–235—5' CCCTGTTAGCCACCC 3'
   Primer 2, nt 802–818—5' TCCACCATCCACTGCAG 3'
2. cfiA:
   Primer 1, nt 551–568—5' CCTTATCTCCATGCTTTT 3'
   Primer 2, nt 1126–1145—5' TTTTCGGCCATGCCGTCACG 3'
3. Arakawa et al.:
   Primer 1, nt 250–267—5' GGCAGATGATTCGCAAAC 3'
   Primer 2, nt 841–858—5' GCATGATTTTCCGGCCAG 3'
4. PBP 2X:
   Primer 1, nt 1450–1470—5' ATGACCCTCCTTGAGCAAAAG 3'
   Primer 2, nt 2038–2056—5' CTACCAACTGAATATCTGA 3'
5. AlgR3:
   Primer 1, nt 8–25—5' TCCGCCTGGAGGCACGTC 3'
   Primer 2, nt 60–76—5' TTGCTGCAACAGGTGCA 3'

Amplification of Target Sequences

The amplification reaction is carried out in a total volume of approximately 100 Al of reaction mixture using a DNA Thermal Cycler for PCR (Perkin-Elmer Cetus). The reaction mixture comprises approximately:

1. 50 mM KCl
2. 10 mM Tris-HCl pH 8.3
3. 1.5 mM MgCl
4. 0.001% w/v gelatin
5. 200 µM of each of three of the four dNTP's
6. 200 µM of biotinylated fourth dNTP
7. 1.0–3.0 units of Taq DNA polymerase
8. the multiple primer pairs (each pair in significant excess)
9. the DNA sample to be tested After denaturation of the target DNA at approximately 93° C. for approximately 1 min., the primer pairs are simultaneously hybridized to their respective target DNA's at approximately 45° C. for approximately 1 min. The hybridized primers are extended by DNA synthesis at approximately 72° C. for 2 min. This step incorporates the biotinylated dNTP into the primer extension products, to be used for later detection.

The cycle of denaturation, annealing and primer extension is repeated approximately 30 times. When the amplification is complete, the remaining primers, dNTP's, etc. are removed by size from the amplification products by filtration in a Centricon-30 Micro-Concentrator (Amicon), which retains single stranded DNA 60 nucleotides or more in length.

Detection of Primer Extension Products

Primer extension products thus obtained are detected by binding to nitrocellulose in a "dot blot" format, and binding a streptavidin-alkaline phosphatase conjugate ("Detek I-alk" available from Enzo Biochem, Inc.) to any biotinylated amplification products which are present. Enzyme bound to primer extension products on the solid support is detected by exposing the enzyme to its substrate and allowing a color reaction to occur. Development of a blue to purple colored precipitate on the surface of the nitrocellulose indicates amplification of at least one of either the target sequences associated with resistance to β-lactam antibiotics or the target sequence associated with *P. aeruginosa*, which is commonly drug resistant.

EXAMPLE 2

Simultaneous Detection of Resistance to Multiple Antibiotics

Two erm genes, conferring resistance to erythromycin, are analyzed for sequence as in Example 1 and primer pairs are selected so that the expected amplified target sequence will be about 300 nucleotides long:

1. Dhillon, et al. (1989) Molecular Microbiology 3: 1405–1414. The ermE gene from *Streptomyces erythraeus*.
   Primer 1, nt 302–323—5' AACGAGGCGTTCGAGGCGGAGT 3'
   Primer 2, nt 585–602—5' CCGCAGGGTGGCCGTAGA 3'
2. Trieu-Cuot et al. (1990) Nucleic Acids Research 18: 3660. The erm gene associated with transposon Tn1545 from *Streptococcus pneumoniae*.
   Primer 1, nt 498–517—5' ATTAGACAGTCATCTATTCA 3'
   Primer 2, nt 783–802—5' CCGCTGGCAGCTTAAGCAAT 3'

The selected primers are synthesized as described in Example 1.

The primers of Example 1, for detecting resistance to β-lactam antibiotics and the presence of Pseudomonas, are expected to prime the amplification of target sequences approximately 600 nucleotides and 70 nucleotides in length, respectively. The erm primers are expected to prime the amplification of target sequences approximately 300 nucleotides in length.

All of the above primers are simultaneously included in the amplification reaction, which is performed according to the protocol of Example 1, except that the cycle is repeated 35 times and additional dNTP's (200 µM each) and primers are added prior to the 30th repetition. Following amplification, the reaction mixture is loaded on a 2.5% agarose gel containing 0.5 µg/ml EthBr and electrophoresed until unreacted primers and dNTP's are removed and the primer extension product bands are separated sufficiently to be identified. Biotinylated molecular weight markers are simultaneously electrophoresed in a parallel lane.

Following electrophoresis, the bands containing primer extension products are transferred to nitrocellulose according to the method of Southern (1975). The nitrocellulose is then developed using the Detek-alk staining system (Enzo), allowing formation of a blue to purple precipitate corresponding to the bands containing biotinylated DNA. The visualized bands in the lane containing amplified target sequences are compared to the molecular weight markers to obtain the approximate size of each band. Comparison of the sizes of the amplification products visualized to the predicted sizes of the expected amplification products reveals only a 300 nucleotide band and a 600 nucleotide band, indicating potential erythromycin and β-lactam resistance but no apparent infection with Pseudomonas.

EXAMPLE 3

Kit For Detecting Resistance To Antibiotics

A kit for simultaneously detecting resistance to β-lactam antibiotics, resistance to erythromycin and the presence of Pseudomonas comprises, in separate tubes, the following components:

1. a mixture of the primer pairs of Example 2 (each primer pair 1.0 μM)
2. dGTP, dTTP and dCTP (20 mM each)
3. biotinylated dATP (20 mM)
4. 10× amplification buffer (500 mM potassium chloride, 100 mM Tris-HCl pH8.3, 15 mM magnesium chloride, 0.01% gelatin)
5. Tap DNA polymerase (300 units/μl)
6. Streptavidin-alkaline phosphatase complex
7. 5-bromo-4-chloro-3-indolyl phosphate
8. Nitroblue tetrazolium
9. nitrocellulose sheets
10. isolated DNA containing the target sequences (positive control)
11. isolated DNA from drug sensitive microorganisms (negative control)

To perform the assay, 10 μl of 10× buffer, 1 μl of each dNTP, 1 μl of biotinylated dATP, 1 μl Taq polymerase and 0.3 μM primers is added to the prepared test sample to form a reaction mixture of 100 μl in a 0.5 ml microcentrifuge tube. A 75 μl mineral oil cap is layered over the reaction mixture. The reaction mixture is placed in a Perkin-Elmer Cetus DNA Thermal Cycler for PCR and the amplification of target sequences is performed as in Example 2.

Similar reactions are performed in parallel using the positive and negative control DNA in place of the prepared sample.

Following amplification, the reaction mixture and positive and negative controls are subjected to agarose gel electrophoresis, Southern blotted, and amplified target sequences are detected as in Example 2.

What is claimed is:

1. A method for detecting genetic elements associated with resistance of an infectious bacteria to an antibacterial drug, the method comprising:
    a) providing a test sample comprising nucleic acid isolated from a clinical specimen;
    b) providing multiple pairs of single stranded oligonucleotide primers selected so that each pair of oligonucleotide primers is complementary to one of a plurality of target sequences of double stranded DNA associated with resistance to an antibacterial drug, said double stranded DNA of each of said target sequences having 3' ends complementary to one of the multiple pairs of oligonucleotide primers provided, and wherein one or more pairs of primers is capable of hybridizing to regions of genetic elements from different sources, and wherein said primer pairs are selected so that target sequences associated with different mechanisms of resistance to an antibacterial drug can be detected, if said target sequences are present in the test sample;
    c) treating the test sample with the primers under conditions such that each primer will hybridize specifically to its target sequence such that any DNA synthesis primed from nonspecific hybridization will not prevent detection of target sequences associated with resistance to the drug;
    d) treating the hybridized primers in a common amplification reaction mixture under conditions such that primer extension products for each pair of oligonucleotide primers are simultaneously synthesized for the sequences to which a primer is hybridized in the common amplification reaction mixture,
    e) repeating steps c) and d) until the target sequences present are sufficiently amplified to be detected;
    f) detecting the amplified target sequences, and,
    g) identifying the amplified target sequences correlated with the genetic elements associated with antibacterial drug resistance.

2. A method for simultaneously detecting genetic elements associated with resistance of an infectious bacteria to multiple antibacterial drugs comprising:
    a) providing a test sample comprising nucleic acid isolated from a clinical specimen;
    b) providing multiple pairs of single stranded oligonucleotide primers selected so that each pair of oligonucleotide primers is complementary to one of a plurality of target sequences of double stranded DNA associated with resistance to the antibacterial drugs, said double stranded DNA of each of said target sequences having 3' ends complementary to one of the multiple pairs of oligonucleotide primers provided, and wherein one or more pairs of primers is capable of hybridizing to regions of genetic elements from difference sources, and wherein said primer pairs are selected so that target sequences associated with resistance to different antibacterial drugs can be detected if said target sequences are present in the test sample;
    c) treating the test sample with the primers under conditions such that each primer pair will hybridize specifically to its target sequence such that any DNA synthesis primed from nonspecific hybridization will not prevent detection of target sequences associated with resistance to the drugs;
    d) treating the hybridized primers in a common amplification reaction mixture under conditions such that primer extension products for each pair of oligonucleotide primers are simultaneously synthesized for the sequences to which a primer is hybridized in the common amplification reaction mixture and the primer extension products associated with resistance to each drug are separately identifiable;
    e) repeating steps c) and d) until the target sequences present are sufficiently amplified to be detected;
    f) simultaneously detecting the amplified target sequences of step e, and,
    h) identifying the amplified target sequences correlated with the genetic elements associated with resistance to each drug.

3. The method according to claims 1 or 2 wherein the target sequences amplified are from genetic elements characteristic of a particular bacteria which is resistant to an antibacterial drug.

4. A method according to claim 3 wherein resistance to an antibacterial selected from the group consisting of β-lactams, quinolones, and macrolides is detected.

5. A method according to claims 1 or 2 further comprising the step of providing at least one pair of primers which is complementary to a target sequence specific for a selected bacteria.

6. A method according to claim 5 wherein a pair of primers is provided which is complementary to a target sequence specific for Pseudomonas.

7. A method according to claims 1 or 2 wherein the primers are derivatized with a detectable label.

8. A method according to claim 7 wherein the primers are derivatized with a label selected from the group consisting of biotin, avidin, radioisotopes, fluorescent molecules and chromogenic enzymes.

9. A method according to claims 1 or 2 wherein synthesis of primer extension products incorporates a detectable label into the primer extension products.

10. A method according to claim 9 wherein a label selected from the group consisting of biotin, avidin, radioisotopes, fluorescent molecules and chromogenic enzymes is incorporated.

11. A method according to claims 1 or 2 wherein the primers are synthesized.

12. A method according to claims 1 or 2 wherein the primers are isolated from naturally occurring or cloned DNA.

13. A method according to claims 1 or 2 wherein the primers are complementary to target sequences associated with genetic elements residing in a nucleic acid sequence present on a plasmid, transportable element, or a chromosome.

14. A method according to claims 1 or 2 wherein the amplified target sequences are detected by means selected from the group consisting of chromogenic enzymes, intercalating dyes, radioisotopes, biotin, avidin and fluorescent molecules.

15. A method according to claim 14 wherein amplified target sequences are detected by means of a chromogenic enzyme selected from the group consisting of horseradish peroxidase and alkaline phosphatase.

16. A method according to claim 14 wherein the amplified target sequences are bound to a solid support prior to detection.

17. A method according to claims 1 or 2 wherein the test sample comprises mRNA and cDNA is synthesized prior to step c).

18. A method according to claims 1 or 2 wherein the amplified target sequences are identified by size.

19. A method according to claim 18 wherein the amplified target sequences are separated into bands by gel electrophoresis.

20. A method according to claim 19 wherein the bands are identified by Southern blotting or staining with ethidium bromide.

21. A method according to claim 18 wherein the amplified target sequences are separated by chromatography.

22. A method according to claim 18 wherein the amplified target sequences are identified by means of separately detectable labels.

23. A method according to claim 22 wherein the target sequences are identified using multiple chromogenic enzymes which are capable of producing reaction products having different colors.

24. A method according to claim 23 wherein two of the reaction products are produced by horse radish peroxidase and alkaline phosphatase.

25. A method according to claim 22 wherein the target sequences are identified using biotin and avidin.

26. A method according to claim 22 wherein the target sequences are identified using radioisotopes having different emission spectra.

27. A method according to claims 1 or 2 wherein the primer pairs are hybridized at 37–55° C.

28. A method according to claims 1 or 2 wherein the hybridized primers are treated with Taq DNA polymerase.

29. A method according to claims 1 or 2 wherein the hybridized primers are treated with at least one deoxyribonucleoside triphosphate derivatized with a detectable label.

30. A method according to claims 1 or 2 wherein steps c) and d) are repeated 10–45 times.

31. A method according to claims 1 or 2 wherein the hybridized primers are treated with approximately 50 mM potassium chloride, 10 mM Tris-HCl pH 8.3, 1.5–4.0 mM magnesium chloride, 0.001% w/v gelatin, 200 $\mu$M of each of the four deoxyribonucleoside triphosphates, and 1.0–3.0 units of Taq DNA polymerase.

32. A test kit for simultaneously detecting multiple genetic elements associated with resistance of an infectious bacteria to an antibacterial drug, the kit comprising:
  a) multiple pairs of single stranded oligonucleotide primers selected so that the oligonucleotides of each pair are complementary to one of a plurality of target sequences of double stranded DNA associated with resistance to an antibacterial drug, said double stranded DNA of each of said target sequences having 3' ends complementary to said multiple pairs of oligonucleotide primers provided, and wherein one or more pairs of primers is capable of hybridizing to regions of genetic elements from different sources, and wherein said primer pairs are selected so that target sequences associated with different mechanisms of resistance to an antibacterial drug can be detected, if said target sequences are present in the test sample;
  b) reagents for DNA synthesis, whereby treatment of a test sample containing nucleic acid with the primers and the reagents results in hybridization of each primer pair to its target sequence and simultaneous amplification of the target sequences to which primers are hybridized.

33. A kit according to claim 32 wherein the target sequences detect resistance to antibacterial selected from the group consisting of β-lactams, quinolones and macrolides.

34. A kit according to claim 32 wherein the reagents for DNA synthesis comprise the four deoxyribonucleoside triphosphates and Taq DNA polymerase.

35. A kit according to claim 32 wherein the reagents for DNA synthesis comprise at least one dNTP derivatized with a detectable label.

36. A kit according to claim 32 further comprising means for detecting amplified target sequences.

37. A kit according to claim 36 wherein the means for detecting comprise labels selected from the group consisting of chromogenic enzymes, radioisotopes, biotin, avidin, intercalating dyes and fluorescent molecules.

38. A kit according to claim 37 further comprising a solid support for detection of amplified target sequences.

39. A kit according to claim 32 further comprising means for identifying amplified target sequences.

40. A kit according to claim 39 wherein the means for identifying comprises a device for separation of the amplified target sequences by size.

41. A kit according to claim 40 further comprising reagents for detection of the separated target sequences.

42. A kit according to claim 39 wherein the means for identifying comprises reagents for separate detection of the amplified target sequences associated with each one of multiple drug resistances.

43. A kit according to claim 42 wherein the reagents for separate detection comprise labels selected from the group consisting of chromogenic enzymes, fluorescent molecules, biotin and avidin and radioisotopes.

44. A kit according to claim 39 wherein the means for identifying comprises reagents for separate isolation of amplified target sequences associated with each drug resistance.

45. A kit according to claim 44 wherein the reagents for isolation comprise biotin and avidin.

46. A kit according to claim 32 wherein the primers are derivatized with a detectable label.

47. A kit according to claim 46 wherein the label is selected from the group consisting of radioisotopes, biotin and avidin.

48. A kit according to claim 32 further comprising at least one primer pair capable of hybridizing to a target sequence specific for a selected microorganism.

49. A kit according to claim 48 wherein the primer pair is capable of hybridizing to a target sequence specific for Pseudomonas.

50. A kit according to claim 32 wherein the primers are synthesized.

51. A kit according to claim 32 wherein the primers are isolated from naturally occurring or cloned DNA.

52. A composition of matter for use in reactions amplifying genetic elements associated with resistance of an infectious bacteria to an antibacterial drug, the composition comprising multiple pairs of single stranded oligonucleotide primers, the oligonucleotides of each pair being complementary to one of a plurality of target sequences of double stranded DNA associated with resistance to the antibiotic drugs, said double stranded DNA of each of said target sequences having 3' ends complementary to one of the multiple pairs of oligonucleotide primers provided, and wherein one or more pairs of primers is capable of hybridizing to sufficiently homologous regions of genetic elements from different sources.

53. A composition of matter according to claim 52 further comprising at least one pair of primers which is complementary to a target sequence specific for a selected bacteria.

54. A composition of matter according to claim 53 wherein the bacteria is Pseudomonas.

55. The method according to claims 1 or 2 wherein the clinical specimen is blood.

56. The method according to claims 1 or 2 wherein the target sequences amplified are from genetic elements associated with a mechanism of resistance independent of the species of the resistant bacteria.

* * * * *

UNITED STATES PATENT AND TRADEMARK OFFICE
CERTIFICATE OF CORRECTION

PATENT NO.    : 6,013,435
DATED         : January 11, 2000
INVENTOR(S)   : Neil J. Nusbaum It is certified that error appears in the above-identified patent and that said Letters Patent is hereby corrected as shown below:

Column 10,
Line 35, "100 Al" should read -- 100 1 --

Column 15,
Line 29, "100 Al" should read -- 100 1 --

Column 19,
Line 61, "nucleoside" should read -- nucleotide --.

Column 20,
Lines 1 and 29, "deoxyribonucleoside" should read -- deoxyribonucleotide --.

Signed and Sealed this

Twenty-third Day of July, 2002

*Attest:*

JAMES E. ROGAN
*Attesting Officer*    *Director of the United States Patent and Trademark Office*

UNITED STATES PATENT AND TRADEMARK OFFICE
CERTIFICATE OF CORRECTION

PATENT NO.    : 6,013,435
DATED         : January 11, 2000
INVENTOR(S)   : Neil J. Nusbaum It is certified that error appears in the above-identified patent and that said Letters Patent is hereby corrected as shown below:

Column 10,
Line 35, "100 Al" should read -- $100 \mu l$ --

Column 15,
Line 29, "100 Al" should read -- $100 \mu l$ --

Column 19,
Line 61, "nucleoside" should read -- nucleotide --.

Column 20,
Lines 1 and 29, "deoxyribonucleoside" should read -- deoxyribonucleotide --.

This certificate supersedes Certificate of Correction issued July 23, 2002.

Signed and Sealed this

First Day of October, 2002

Attest:

JAMES E. ROGAN
Attesting Officer    Director of the United States Patent and Trademark Office